(12) United States Patent
Staal et al.

(10) Patent No.: US 9,410,924 B2
(45) Date of Patent: Aug. 9, 2016

(54) TEST CHIP WITH PLUG FOR MEASURING THE CONCENTRATION OF AN ANALYTE IN A LIQUID, HOUSING FOR TEST CHIP AND SOCKET FOR PLUG

(75) Inventors: Steven Selwyn Staal, Enschede (NL); Jan Floris, Enschede (NL); Marko Blom, Enschede (NL); Johannes Oonk, Enschede (NL)

(73) Assignee: CE-MATE B.V., Enschede (NL)

( * ) Notice: Subject to any disclaimer, the term of this patent is extended or adjusted under 35 U.S.C. 154(b) by 927 days.

(21) Appl. No.: 12/600,738

(22) PCT Filed: May 18, 2007

(86) PCT No.: PCT/EP2007/004468
§ 371 (c)(1),
(2), (4) Date: Apr. 30, 2010

(87) PCT Pub. No.: WO2008/141659
PCT Pub. Date: Nov. 27, 2008

(65) Prior Publication Data
US 2010/0236926 A1    Sep. 23, 2010

(51) Int. Cl.
*G01N 27/447*    (2006.01)
*H01R 24/00*    (2011.01)
*B01L 9/00*    (2006.01)
(Continued)

(52) U.S. Cl.
CPC ...... *G01N 27/4473* (2013.01); *B01L 3/502715* (2013.01); *G01N 27/44743* (2013.01); *B01L 3/50273* (2013.01); *B01L 9/527* (2013.01); *B01L 2200/027* (2013.01); *B01L 2200/04* (2013.01); *B01L 2200/10* (2013.01);
(Continued)

(58) Field of Classification Search
CPC .......... B01L 3/50273; B01L 3/502715; B01L 2200/027; B01L 2200/10; B01L 2200/04; B01L 2300/0645; B01L 2300/0861; B01L 2400/0421; G01N 27/4473; G01N 27/44743
USPC .......... 204/450, 549, 600; 422/500, 502, 554, 422/560, 565-566
See application file for complete search history.

(56) References Cited

U.S. PATENT DOCUMENTS 3,506,554 A    4/1970 Broome
4,242,194 A    12/1980 Steiner et al.
(Continued)

FOREIGN PATENT DOCUMENTS

CA    2737892    9/2003
DE    20 2005 009 960    9/2005
(Continued)

OTHER PUBLICATIONS

Japanese Official Action issued in Application No. 2009/537484 on May 12, 2011.
(Continued)

*Primary Examiner* — Jennifer Wecker
(74) *Attorney, Agent, or Firm* — Stephen H. Eland; Dann, Dorfman, Herrell & Skillman, P.C.

(57) ABSTRACT

Measurement device (10) for taking a liquid sample, comprising: a measurement portion (15) with a measurement surface (20), for being in use contacted with the liquid surface and a plug portion (40) having a plurality of electrical contacts (50), wherein the plug portion (40) is mountable to a socket (110) of a measurement evaluation apparatus (100).

27 Claims, 8 Drawing Sheets

(51) Int. Cl.
*B01L 3/00* (2006.01)
*B23P 17/04* (2006.01)

(52) U.S. Cl.
CPC . *B01L 2300/0645* (2013.01); *B01L 2300/0861* (2013.01); *B01L 2400/0421* (2013.01); *Y10T 29/49826* (2015.01)

(56) References Cited

U.S. PATENT DOCUMENTS

| | | | |
|---|---|---|---|
| 4,415,418 A | | 11/1983 | Turre et al. |
| 4,956,062 A | | 9/1990 | Ooi et al. |
| 5,223,114 A | | 6/1993 | Zare et al. |
| 5,849,208 A | * | 12/1998 | Hayes et al. ............... 216/94 |
| 5,882,496 A | | 3/1999 | Northrup et al. |
| 5,900,130 A | | 5/1999 | Benvegnu et al. |
| 5,955,028 A | * | 9/1999 | Chow ........................ 422/63 |
| 5,989,402 A | | 11/1999 | Chow et al. |
| 6,090,545 A | | 7/2000 | Wohlstadter et al. |
| 6,258,254 B1 | | 7/2001 | Miyamoto et al. |
| 6,399,025 B1 | | 6/2002 | Chow |
| 6,432,720 B2 | | 8/2002 | Chow |
| 6,444,474 B1 | * | 9/2002 | Thomas et al. ............. 436/146 |
| 6,503,757 B1 | | 1/2003 | Chow |
| 6,730,199 B1 | * | 5/2004 | Hänni et al. ............ 204/403.02 |
| 6,864,480 B2 | | 3/2005 | Staats |
| 7,217,352 B2 | | 5/2007 | Seino et al. |
| 7,494,622 B2 | * | 2/2009 | Picollet-Dahan et al. . 422/82.01 |
| 8,202,492 B2 | * | 6/2012 | Linder .................. B01L 3/5027 422/50 |
| 2002/0025576 A1 | | 2/2002 | Northrup et al. |
| 2002/0027075 A1 | | 3/2002 | Manz et al. |
| 2003/0068646 A1 | * | 4/2003 | Singh et al. ................. 435/7.1 |
| 2003/0114785 A1 | | 6/2003 | Kikuchi et al. |
| 2003/0209314 A1 | | 11/2003 | Guo et al. |
| 2004/0037739 A1 | * | 2/2004 | McNeely et al. ............... 422/58 |
| 2004/0086872 A1 | * | 5/2004 | Childers et al. ................. 435/6 |
| 2004/0089546 A1 | * | 5/2004 | Bahatt et al. ................. 204/450 |
| 2004/0126279 A1 | * | 7/2004 | Renzi ............... B01L 3/502715 422/502 |
| 2005/0135968 A1 | | 6/2005 | Augstein |
| 2005/0150766 A1 | | 7/2005 | Manz et al. |
| 2005/0268701 A1 | | 12/2005 | Hintsche |
| 2005/0279635 A1 | * | 12/2005 | Chow et al. .................... 204/601 |
| 2006/0204143 A1 | | 9/2006 | Shiota et al. |
| 2007/0051628 A1 | | 3/2007 | Dolnik |
| 2007/0053796 A1 | * | 3/2007 | Gau et al. ...................... 422/100 |
| 2007/0065346 A1 | * | 3/2007 | Henry et al. .................. 422/100 |
| 2009/0302190 A1 | * | 12/2009 | Trieu et al. .................... 248/683 |
| 2010/0062082 A1 | * | 3/2010 | Staal et al. .................... 424/722 |

FOREIGN PATENT DOCUMENTS

| | | |
|---|---|---|
| EP | 215419 | 3/1987 |
| EP | 0295942 | 12/1988 |
| EP | 0631133 | 12/1994 |
| EP | 1016864 | 7/2000 |
| EP | 1413879 | 4/2004 |
| EP | 1486778 | 12/2004 |
| EP | 952890 | 6/2005 |
| EP | 1543935 | 6/2005 |
| EP | 1553395 | 7/2005 |
| FR | 2844052 | 3/2004 |
| JP | 62069139 | 3/1987 |
| JP | 1158342 | 6/1989 |
| JP | H04501768 | 3/1992 |
| JP | H053998 | 1/1993 |
| JP | H0552799 | 3/1993 |
| JP | 10311827 | 11/1998 |
| JP | 2000002677 | 1/2000 |
| JP | 2000227414 | 8/2000 |
| JP | 2000515630 | 11/2000 |
| JP | 2001258868 | 9/2001 |
| JP | 2002527250 | 8/2002 |
| JP | 2002544494 | 12/2002 |
| JP | 2003530566 | 10/2003 |
| JP | 2004020367 | 1/2004 |
| JP | 2004109082 | 4/2004 |
| JP | 2005331411 | 2/2005 |
| JP | 2005134190 | 5/2005 |
| JP | 2006047321 | 2/2006 |
| JP | 2007-006858 | 1/2007 |
| JP | 2007-064742 | 3/2007 |
| KR | 20000066685 | 11/2000 |
| WO | 96/33405 | 10/1996 |
| WO | 98/05424 | 2/1998 |
| WO | 00/67907 | 11/2000 |
| WO | 01/77641 | 10/2001 |
| WO | 03/012421 | 2/2003 |
| WO | 2005/003724 | 2/2005 |
| WO | 2005/094286 | 10/2005 |

OTHER PUBLICATIONS

Tjerkstra et al, "Multi-Walled Microchannels: Free-Standing Porous Silicon Membranes for Use in µTAS", Journal of Microelectromechanical Systems, Dec. 2000, pp. 495-501, vol. 9, No. 4.
Invitation to Pay Additional Fees, European Patent Office Form PCT/ISA/2006, Nov. 27, 2007.
Partial International Search Report, European Patent Office Form PCT/ISA/2006 (Annex), Nov. 27, 2007.
Vrouwe, et al, "Direct Measurement of Lithium in Whole Blood Using Microchip Capillary Electrophoresis with Integrated Conductivity Detection", Electrophesis, vol. 25, 2004, pp. 1660-1667.
Vrouwe et al, "Microchip Analysis of Lithium in Blood Using Moving Boundary Electrophesis and Zone Electrophoresis", Electrophoresis, 2005, vol. 26, pp. 3032-3042.
ReliaLAB, Insta Read Lithium System Information Sheet, Jun. 2005, 7 pages.
Eurasian Search Report issued in Eurasian Application No. 200901553/26 on Oct. 13, 2010.
Extended European Search Report issued in European Patent Application No. 12175953.4 on Jan. 14, 2013.
Extended European Search Report issued in European Application No. 12183414.7 on Jan. 30, 2013.
Extended European Search Report issued in European Application No. 12183414.7 on Feb. 6, 2013.
Official Action issued in EP Application No. 12183415.4 on Oct. 22, 2013.
Official Action issued in JP Application No. 2013-069912 on Apr. 8, 2014.
Official Action issued in JP Application No. 2013-069913 on Apr. 8, 2014.

* cited by examiner

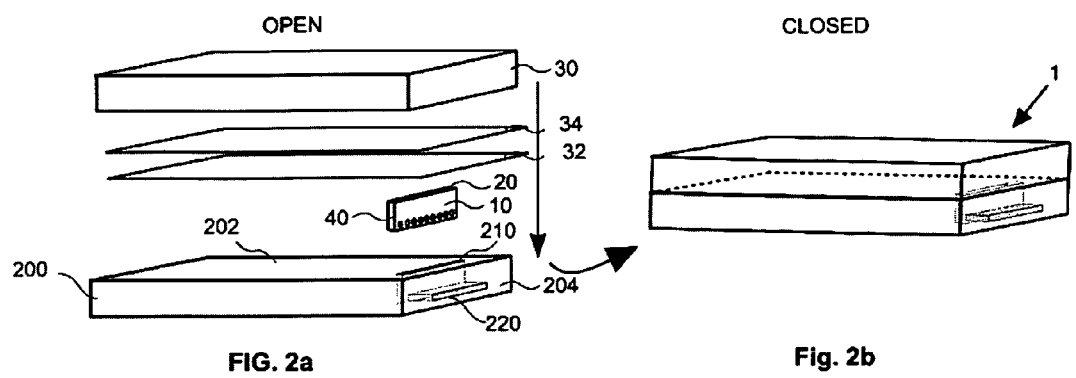
FIG. 2a
Fig. 2b
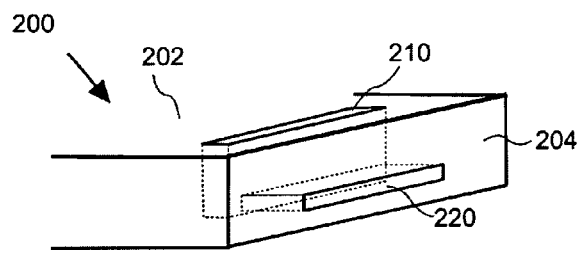
FIG. 2c

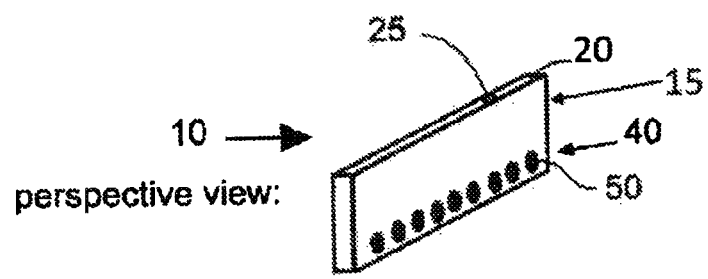
FIG. 3a perspective view:
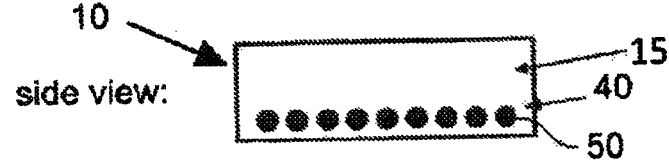
FIG. 3b side view:
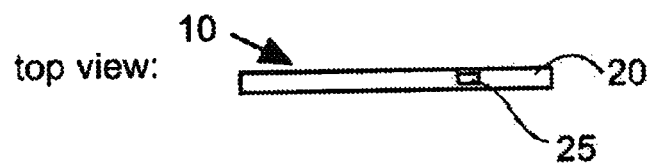
FIG. 3c top view:

US 9,410,924 B2

TEST CHIP WITH PLUG FOR MEASURING THE CONCENTRATION OF AN ANALYTE IN A LIQUID, HOUSING FOR TEST CHIP AND SOCKET FOR PLUG

CROSS-REFERENCE TO RELATED APPLICATIONS

This application is a 371 application of International Patent Application No. PCT/EP2007/004468 filed on May 18, 2007 and is related to U.S. patent application Ser. No. 12/515,635 filed on May 20, 2009 which is based on International Patent Application No. PCT/EP2006/11148 filed on Nov. 21, 2006.

FIELD OF THE INVENTION

The invention relates to sensors for components in liquid samples. In particular, the invention relates to sensors for evaluating charged species concentrations, in particular ion concentrations, for example lithium ion concentrations, in samples, such as blood that can be easily handled by a user, i.e. a patient.

BACKGROUND AND RELATED ART

Inorganic ions are an essential requirement for life and are found in large amounts in drinking water, blood and cells of an organism as well as in the environment. For example, the presence of many ions, e.g. sodium, potassium, magnesium, and calcium, inside and outside of the cells is essential for a living organism. Consequently, a measurement of the ion concentration in the blood and in blood cells of animals and human beings is of high importance for a large variety of body functions.

Normally lithium is not at all or solely as a trace element present in the blood plasma, but it is also used as a drug to treat bipolar mood disorder. It is estimated that worldwide over one million people take lithium on a daily basis. A disadvantage in the use of lithium is the very low therapeutic index, i.e., the ratio between the toxic concentration and the therapeutic concentration. Most patients respond well to a blood plasma concentration of 0.4-1.2 mmol/L lithium while a lithium concentration of above 1.6 mmol/L is considered toxic. A prolonged high blood lithium level can result in permanent damage to the nervous system and even death. Monitoring of the lithium concentration during treatment is therefore essential, with regular checks every couple of months to keep the lithium level at desired level.

The direct measurement of lithium in whole blood and the determination of inorganic cations in blood plasma have been described and demonstrated by E. Vrouwe et al. in *Electrophoresis* 2004, 25, 1660-1667 and in *Electrophoresis* 2005, 26, 3032-3042. Using microchip capillary electrophoresis (CE) with defined sample loading and applying the principles of column coupling, the concentration of alkali metals in the blood was determined in a drop of whole blood. Blood collected from a finger stick was transferred onto a chip without extraction or removal of components from the blood. The lithium concentration can be determined in the blood plasma from a patient on lithium therapy without sample pre-treatment. Using a chip with conductivity detection, a detection limit of 0.1 mmol/L has been obtained for lithium in a 140 mmol/L sodium matrix.

In these disclosures, the components of the blood sample are separated electrophoretically inside a micro-channel. A double T injection geometry is used to select the ion components of interest and to guide them to detection electrodes.

A method and an apparatus for measuring the ion concentration in liquid samples is disclosed in the co-pending PCT application PCT/EP2006/011148 the teachings of which are included by reference herewith. This PCT application describes an apparatus for the measurement of a concentration of a charged species in a sample, the sample comprising a plurality of types of charged species and at least one insoluble component, the apparatus comprising at least one channel with at least one opening with a filter function, at least two electrophoresis electrodes arranged along the at least one channel, and at least one sensor for measuring at least one type of charged species in the at least one channel.

The dimensions of the opening and the channels used in such an apparatus are usually very small in order to reduce the amount of liquid necessary and the size of the apparatus. Typical channel dimension are in the order of less than 1 cm in width and less than 100 µm in depth. Consequently the apparatus can be quite small as well in order to minimize the amount of material used for the apparatus. The material is often expensive as for example glass.

The apparatus should also be easily usable by a patient or other user. In particular, the patients suffering from bipolar mood disorder or similar illnesses, often suffer from quivering or shaking hands and encounter problems in handling small pieces.

Furthermore blood sample and consequently the channels can be easily contaminated by blood or other liquids and can not be reused without intensive cleaning and sterilisation.

In contrast, the known prior measurement devices are complex microfluidic and electronic components that are expensive and therefore not suited for one-time use only.

It is an object of the present invention to provide a device and a method for easy handling of liquid sample measurement devices for measuring small samples.

It is a further object of the invention to provide measurement devices that can be used as disposables while advanced measurement techniques can be employed.

SUMMARY OF THE INVENTION

These and other objects of the invention are met by a measurement sample handling device and a method for taking a liquid sample according to the invention, wherein the measurement sample handing device comprises a measurement device and a handling unit.

The measurement device for taking the liquid samples comprises: a measurement portion with a measurement surface for being in use contacted with the liquid sample and a plug portion having a plurality of electrical contacts, wherein the plug portion is mountable to a socket of a measurement evaluation apparatus. The measurement surface may be arranged at a different position of the measurement device than the plug portion in order to avoid liquid of the liquid sample to come into contact with the electrical contacts. In particular, the plug portion may be arranged at a different side of the measurement device, than the measurement surface.

The measurement surface and the measurement portion may be made form the same material, for example from glass and may be realized in one piece. The measurement device may further comprise a plurality of electrodes coupled to the electrical contacts. The measurement device may neither have any active electrical components, such as switches, transistors nor an electrical power supply. In some cases the measurement device may comprise some passive electrical components such as temperature sensors or the like.

During assembly, the measurement device might be inserted into a handling unit the handling unit having a first opening for the measurement surface and at least a second opening for the plurality of electrical contacts. Thus when inserted into the handling unit, the measurement surface is accessible by a user or patient for placing a liquid sample. On the other side the plug portion is accessible through the second opening of the handling unit for allowing access to the electrical contact, for example by a socket. Thus, the handling unit may form an electrical contact seal for preventing liquid to come into contact with the electrical contacts at the plug portion of the measurement device.

The handling unit may not comprise any electrical components as all electrical contacts are provided by the measurement device. In some cases, however, the handling unit may comprise electrical contacts and electrical components.

The handling unit may be substantially large in size than the measurement device. Thus the handling unit can be of handy size for easy and safe handling of the measurement sample handling device even by patients suffering from shaking hands or similar. In the same time the measurement device can be kept small in order to minimize the amount of liquid sample necessary for reliable measurements. In addition the smaller measurement devices may be cheaper to produce. The measurement sample handling device can thus be a disposable device that is for few time or one-time use. This is in particular useful if the liquid sample is a body fluid such as blood or another sample that requires sterile and/or clean environment.

The handling unit may also be adapted to accommodate a plurality of measurement devices, for carrying out a plurality of sample measurements in a row or in parallel.

The measurement device may also be positioned at a particular side of the handling unit, for example such that the second opening provides in use easy access to the plug portion from the outside, for example by a plurality of electrical pins, when the measurement sample handling device is inserted into a socket of a measurement evaluation device. The plurality of electrical pins may be arranged to come into electrical contact with the plurality of electrical contacts of the measurement device, when the measurement device or the measurement sample handling device is mounted to the socket.

The measurement evaluation device for evaluating at least one parameter of the liquid sample may comprise a power supply for the measurement device and all further electric and electronic means to carry out a measurement for evaluating the at least parameter. In particular, the measurement evaluation device may comprise control means for controlling and monitoring the electrodes in the measurement device, when the measurement device is inserted into the socket.

The invention also comprises a method for evaluating at least one parameter of a liquid sample comprising: placing the liquid sample on a measurement surface of a measuring device, wherein the measuring device has a plurality of electrical contacts, inserting the measuring device into a socket having a plurality of electrical pins such that at least some of the plurality of electrical pins come into contact with at least some of the plurality of electrical contacts, and determining the at least one parameter by electrical measurements.

The measurement device may also be part of a measurement sample handling device and comprise a handling unit.

The method can be advantageously applied by patient or elderly users, even with shaking hands. A liquid sample, such a blood sample or another body fluid is placed on the measurement surface prior to insertion of the measurement device into the socket. Thus, no electrical power is present in the measurement device when handling the liquid sample. Furthermore, a measurement of the liquid sample can only be started once placing of the sample on the measurement surface has been finished. In some cases, the measurement surface may be concealed by a closure device to protect the liquid sample and/or to prevent evaporation.

The invention also comprises a method for the assembly of the measurement sample handling device, the method comprising: filling at least one channel in a measurement device having a measurement surface and a plug portion, with a solution, the at least one channel having at least one channel opening in the measurement surface, inserting the measurement device into an opening of a handling unit, such that the measurement surface of the measurement device is accessible, and closing the channel opening with a protective layer to be removed prior to use of the measurement device.

This allows for easy fast and cheap production of the measurement sample handling device.

The insertion of the measurement device into the handling unit may be performed through the first opening. The measurement device may also be inserted through a third opening, for example on the opposite side of the handling unit. The second opening may also be enlarged or combined with the third opening to enable insertion of the measurement device into the handling unit.

Inserting the measurement device into the opening of the handling unit and closing or sealing the channel opening which may be performed directly after filling the at least one channel in order to prevent evaporation of the liquid.

The measurement environment may also be kept in a wet or humid environment prior to closing or sealing the channel opening may be performed directly after removing the measurement device from the wet or humid environment.

The at least one channel in the measurement device may be filled with a solution prior to use. The solution may be an electrolyte solution (BGE). The solution may also comprise an electroosmotic flow suppressing substance or a dynamic coating such as poly vinyl alcohol (PVA).

The term prior to use is in this respect understood as being prior to use of the measurement sample handling device by a patient or a user. Prior to use may also include prior to shipment to the user or the patient.

DESCRIPTION OF THE DRAWINGS

The invention may be better understood with respect to the figures and the detailed description of preferred embodiments, which is illustrative only and not limiting to the invention and wherein:

FIGS. 2a to 2c show the disposable device according to the invention in an exploded view, assembled and a portion of the disposable device in greater detail.

FIGS. 3a, 3b, and 3c show the measurement device in a perspective view, side view and top view, respectively.

In the figures same reference numerals describe the same or similar objects.

DETAILED DESCRIPTION OF THE INVENTION

Figure 1:
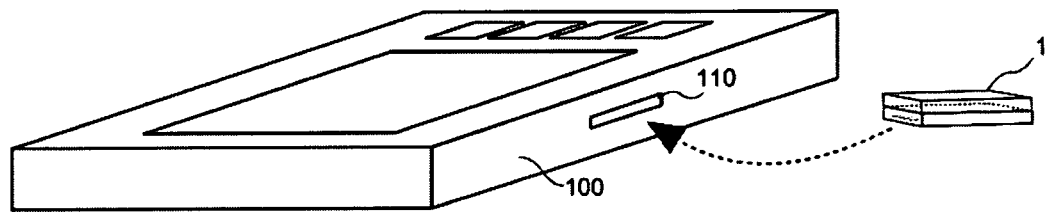
FIG. 1 shows a measurement system according to the invention comprising a measurement evaluation device with a socket for a measurement sample handling device comprising a handling unit and a measurement device.

FIG. 1 shows a measurement system comprising a combination of a measurement evaluation apparatus 100 having a socket 110 and a measurement sample handling device or disposable device 1 comprising a measurement device 10 (shown in FIG. 2a) attachable to the socket 110. The measurement evaluation apparatus 100 comprises electronics for computing and evaluating a species ion concentration taken from a sample in the measurement sample handling device 1. The measurement evaluation apparatus 100 may comprise controls for controlling and checking the measurement and evaluation process. The measurement evaluation apparatus 100 may also comprise indication means, such as a display or similar, to indicate results and setting of the measurement system to a user. The indication means is not shown in the figure. The measurement evaluation apparatus 100 may also comprise interfaces for connecting the measurement system to a computer or a clinical data system (not shown) for data transfer and measurement system control. The measurement evaluation device 110 may also be a personal computer equipped with a socket 110 for receiving the measurement sample handling device 1.

The measurement sample handling device may be a onetime use disposable that is only used for one measurement. The disposable device may, however, also be used for several times, for example for repetitive or parallel measurements. The terms disposable device and measurement sample handling device are used as synonyms within this disclosure.

FIGS. 2a to 2c show the measurement sample handling device 1 in more detail. In FIG. 2a an exploded view is illustrated, an assembled view is illustrated in FIG. 2b and in FIG. 2c the portion of the measurement sample handling device 1 that can be attached to the socket 110 is illustrated in greater detail. The measurement sample handling device 1 also comprises a handling unit 200. The handling unit 200 has a first opening 210 on a first side 202, defined to be the measurement side, and a second opening 220 at a second side 204 of the handling unit 200 as illustrated in FIGS. 2a and 2c. The second surface 204 faces towards the socket 110 of the measurement evaluation device 100 when the measurement sample handling device 1 is mounted in the measurement evaluation apparatus 100. The first opening 210 and the second opening 220 may also be arranged at the bottom face, at the edge of the bottom face and the second face 204 of the handling unit 200 or at any other side of the handling unit 200. The openings may also be enlarged in size to enable the insertion of the measurement device 20 into the handling unit 200.

The first opening 210 and the second opening 220 are interconnected inside the handling unit 200 as illustrated by the dotted lines in FIGS. 2a and 2c.

The measurement device 10 is inserted into the first opening 210 of the handling unit 200. The measurement device 10 has a measurement surface 20 and a plug portion 40. The measurement device 10 may also be inserted through second opening 220 or a third opening 230 as will be explained with respect to FIGS. 9 and 12a,b. The measurement surface 20 is substantially in the same plane as the first side 202 of the handling unit 200 when the measurement device 10 is inserted in the handling unit 200. Thereby, the plug potion 40 is accessible from the outside of the measurement sample handling device 1 through the second opening 220 of the handling unit 200. The measurement device 10 is described in further detail below with respect to FIG. 3.

The measurement device 10 may be made from a different material that the handling unit 200. In particular, the measurement device 10 may be made partially or completely from glass material, whilst the handling unit 200 is made from plastics material.

The measurement device 10 may also be formed from polymer material.

The measurement device 10 is much smaller in size than the handling unit 20. Thus millimeter dimensions of the measurement device 10 may be implemented, while the measurement device 10 can be easily handled with the handling unit 200. The size of the handling unit 200 can be adapted to the needs of the user (patient). For example, the handling unit 200 may have dimensions that provide an easy handling even with shaking hands. For example, the size of the handling unit 200 may be larger than 1 cm, in particular about 4 cm or more in at least one dimension. In addition, at least the second side 204 of the handling unit 200 is adapted to fit into the socket 110. The side faces or other geometrical parameters of the handling unit 200 may also be adapted to fit into the socket 110.

The socket 110 and the handling unit 200 may be formed in a way that there is only one possibility of inserting the disposable or measurement sample handling device 1 comprising the handling unit into the socket 110. Thereby faulty operation by unexperienced or elderly users or patients can be excluded and measurement errors can be avoided.

The measurement device 10 may be arranged close to the second side 204 when inserted inside the handling unit 200. Thus, the measurement device is close to the socket 110 when the measurement sample handling device 1 is inserted into the socket 110. The measurement device 10 may be arranged inside the handling unit 200 such that side of the measurement device 10 comprising the plug portion 40 is parallel to the second side 204 when inserted into handling unit 200.

The handling unit 200 and the measurement surface 20 might be covered by a permeable layer 32 (as seen clearly in FIG. 2a) for providing access to the measurement surface 20 of the measurement device 10. The permeable layer 32 may completely or partially cover the measurement side 202 and the measurement surface 20.

A sealing 34 is provided on top of the measurement side 202 for sealing the permeable layer 32 or the measurement surface 20 for preventing leakage or evaporation of fluids. The sealing layer 34 may be removed by the patient or user prior to use of the measurement device. The permeable layer 32 and the sealing 34 may be of different size. A person skilled in the art will understand that more or fewer layers may be arranged on top of the measurement surface 20 or the first surface 202.

A closure device 30 may be used for closing the measurement surface 20 prior to and/or after use. The sealing 34 and permeable layer 32 may be attached to the measurement device 10, the closure device 30 or to the handling unit 200.

The handling device 200 and the closure device 30 may be made from the same material, for example plastics material. The handling device 200 and the closure device 30 may also be made in one piece. An integral hinge may be provided for separating the closure device portion form the handling device portion and for enabling folding of the closure device on top of the handling device in order to conceal or close the measurement surface 20.

FIGS. 3a, 3b, and 3c show the measurement device 10 in a perspective view, a side view and a top view, respectively.

The measurement device 10 has a first opening 25 in the measurement portion 15. A microfluidic channel 60 (shown in FIG. 4) is implemented in the measurement portion 15 inside the measurement device 10. The first opening 25 provides an access from the surroundings of the measurement surface 20 to the microfluidic channel 60. A person skilled in the art will understand that a plurality of openings 25 can be provided and that the microfluidic channel 60 can comprise a network of different ones of the channels 60 which are realized in the measurement device 10. An example for a channel 60 with a first opening 25, that is particularly useful with the present invention can be found in the patent application PCT/EP2006/011148. The measurement device 10 may be at least partially formed in glass material or another material that can be microstructured.

The first opening 25 may be in the measurement surface 20. The first opening 25 may also be in another side of the measurement portion 15 of measurement device 10 in close proximity to the measurement surface 20 to which the liquid sample is applied. In this case the liquid sample will go from the measurement surface 20 to the first opening 25

The plug portion 40 is arranged at a different side of the measurement device 10 than the measurement surface 20 comprising the first opening 25. Thus, when inserted into the handling unit 200, the plug portion 40 is only accessible through the second opening 220 of the handling unit 200 while the measurement surface 20 is solely accessible through first opening 210 of the handling unit 200. The handling unit 200 may thus provide a seal that ensures that the liquid sample that is in use added to the measurement surface 20 can not come into contact with any of the plurality of electrical contacts 50. Thus, electrical short-circuits between two or more of the plurality of contacts 50 that would impair a measurement or control of functions of the measurement device 10 can be advantageously excluded.

The plug portion 40 and the measurement surface 20 may also be arranged on the same side of the measurement device 10. However, the plug portion 40 and the measurement surface 20 are separated form each other by a sealing portion of the handling unit 200 when the measurement device 10 is inserted into the handling unit 200. Thus, liquids on the measurement surface 20 are prevented from coming into contact with electrical contacts of the plug portion 40.

Figure 4:
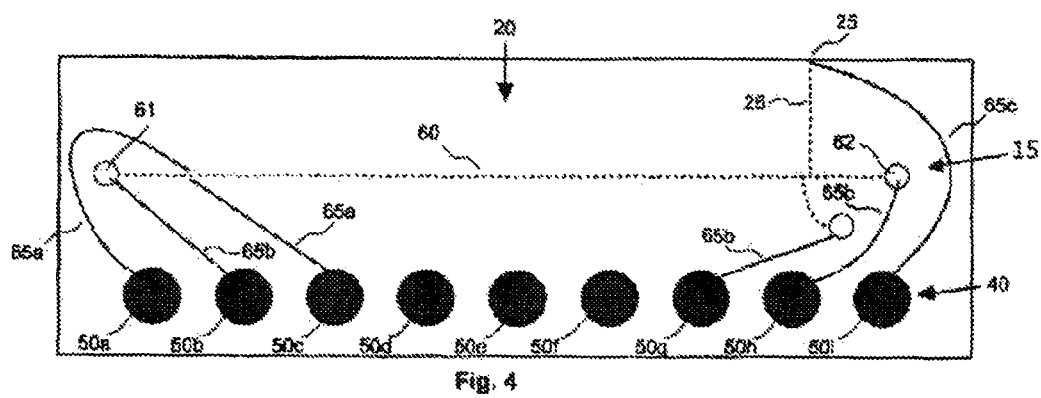
FIG. 4 shows a schematic view of the measurement device in greater detail.

FIG. 4 shows a schematic view of the measurement device 10 in the view of FIG. 3b in greater detail. The microfluidic channel 60 is arranged between two microfluidic reservoirs 61 and 62. The microfluidic channel 60 further has the first opening 25 in the measurement surface 20. The first opening 25 may be connected via a sample channel 26 with the microfluidic channel 60.

In addition, electrodes 65 may be integrated in the measurement device 10. The electrodes 65 may be constructed as electrophoresis electrodes 65b and 65c for separating charged species in the sample inside the microfluidic channel 60. An electrophoresis electrode 65b may be integrated in each ones of the reservoirs 61, 62, 64. The reservoirs 61, 62, 64 may be closed, such that the microfluidic channel 60 provides the only access to the reservoir 61, 62 64 In this way the liquid inside the reservoir is prevented from evaporation and gas formation. The reservoirs 61, 62, 64 may be substantially larger in size that the width, height or depth of the microfluidic channel 60.

Each ones of the electrodes 65b are in electrical contact via electrical path with electrical contact 50b, 50h and 50g, respectively. Thus electrophoresis inside the microfluidic channels 60 can be controlled by applying voltages independently to each ones of the electrophoresis electrodes 65b by the measurement evaluation device 100 when the measurement device 10 is attached to the socket 110. The opening electrode 65c may be integrated at the first opening 25 and connected with electrical contact 50i. The opening electrode 65c may also serve as an electrophoresis electrode or as a control electrode as will be explained later.

The electrodes 65 may also be provided as conductivity electrodes 65a for measuring the conductivity in a section of the microfluidic channel 60 for determining a charge concentration in this section of the microfluidic channel 60. The conductivity electrodes 65a are connected to and addressed by electrical contacts 50a and 50d (as illustrated in FIG. 4) and thus controlled by measurement evaluation device 100 when the measurement device 10 is attached to the socket 110.

The electrophoresis electrodes 65b in capillary electrophoresis system may be based on material that can adsorb hydrogen atoms due to its intrinsic characteristics, for instance palladium or platinum. The adsorption makes it possible to prevent gas formation for example of hydrogen near the electrophoresis electrode 65b used as a cathode.

The use of palladium or platinum as material is in particular useful for the electrophoresis electrode 65b used as a cathode but the other ones of the electrodes 65 may also be made from the same material.

The electrophoresis electrode 65b and/or the opening electrode 65c used as anode may also be made from a different material in order to prevent oxygen gas formation. For instance, the electrophoresis electrode 65b used as anode may be a silver/silver chloride electrode or may be made from copper. In this case, chloride and solid silver or copper ions will be formed instead of oxygen.

Palladium, platinum, nickel, silver/silver chloride and/or copper as well as further materials may also be mixed in one or more of electrodes 65 to combine the advantages of each material.

One or more of the electrodes 65, 65a, 65b, 65c may also be provided with an adhesive layer made from en inert metal such as tantalum or chrome.

The measurement device 10 may further comprise electric components, such as temperature sensors, pH sensors and others that may be electrically contacted and controlled with the remaining electrical contacts 50c, 50c and 50f. It is obvious to a person skilled in the art that the number of the plurality of electrical contacts 50, 50a to 50i is purely exemplary and that more or less electrical contacts can be provided within the scope of the invention.

It is an advantage of the present invention that the measurement device 10 can comprise solely passive electrical components such as wires, conductors and electrodes. No active component, such as transistors, diodes, flip-flops or similar other active electronic components are necessary. The measurement device 10 may be electronically controlled by the measurement evaluation device 100. However, sensors may be integrated into measurement device 10 that can comprise semiconductor elements that may also be active semiconductor elements in some cases.

Figure 5:
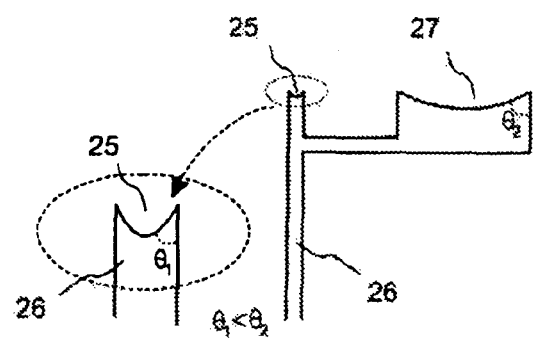
FIG. 5 shows a detailed view of a specific embodiment of two openings of the measurement device.

FIG. 5 shows a detailed view of a specific embodiment of the first opening 25 of the measurement device 20 that is connected to the microfluidic channel 60 by the sample channel 26. In addition, a second opening 27 may be provided, for example to prevent evaporation of fluids. The second opening 27 is fluidly connected to the sample channel 26 and the first opening 25. The second opening 27 may be substantially larger in size than the first opening 25. The difference in size results in different contact angles $\square_1$ and $\square_\square$ at first opening 25 and second opening 27, respectively, when a liquid is filled into the microfluidic system and sample channel 26. The difference in the contact angle $\square_1$ and $\square_\square$ will result in a pressure difference in the first opening 25 and the second opening 27 that will, when the liquid is allowed to evaporate from the first opening 25 and the second opening 27, result in the level of the liquid remaining at essentially the same level in first opening 25 while the liquid level goes down in second opening 27 due to evaporation.

A person skilled in the art will understand that further openings with different of identical sizes can be added on order to modify the evaporation behaviour at the first opening 25.

Figure 6:
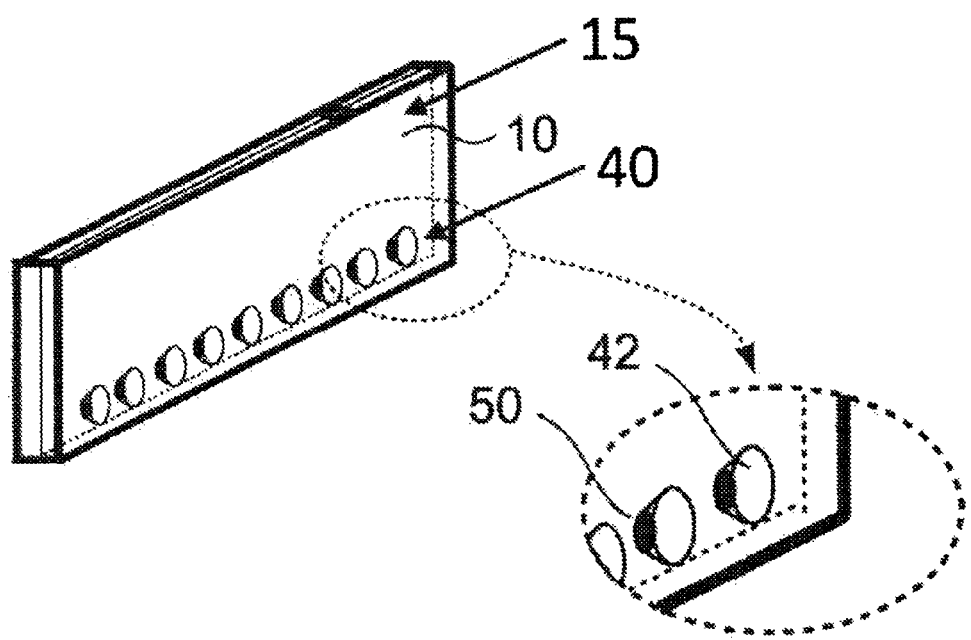
FIG. 6 shows the plurality of electrical contacts of the measurement device according to the invention in more detail

FIG. 6 shows the plurality of electrical contacts 50 in more detail. Each of the plurality of electrical contacts 50 may be arranged inside a hole 42 formed in the plug portion 40 of the measurement device 10. For example an electrical contact may be provided at the bottom of the hole 42. As illustrated each one of the plurality of electrical contacts 50 will be positioned in a separate hole 42. In some cases, two or more of the plurality of electrical contacts 50 may also be arranged together in a single one of the holes 42. In some cases, holes 42 may be provided without any contacts in case the measurement device 10 provides only some functionality. For example, the electrical contacts 50d, 50e and 50f shown in FIG. 4 may be left out if no further electrical component are used. However, the plug portion provides corresponding holes 42 providing space for the corresponding pins of the socket 110.

The hole 42 may be round and of cylindrical shape or conical shape or have any other shape known to a person skilled in the art. The conical shape may be used to align or guide pins of the socket 110 towards each of the plurality of contacts 50. Other shapes of the holes 42 may also be implemented within the scope of the invention.

Furthermore, the layout or arrangement of the electrical contacts may be varied and is by no means limited to the line-arrangement illustrated in the Figures.

It is a feature of the present invention that all electrical contacts of the measurement sample handling device 1 are arranged in the measurement device 10 and that the handling unit 200 does not comprise any electrical components, such as contacts, wiring etc.

Figure 7:
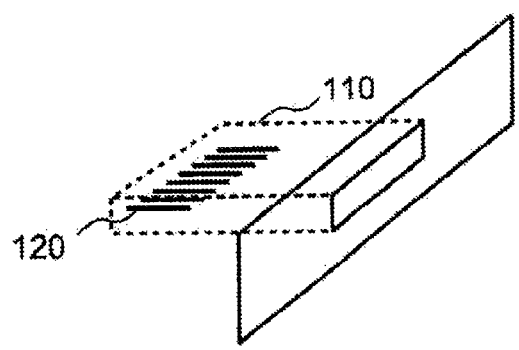
FIG. 7 shows the socket of measurement evaluation device in greater detail.

FIG. 7 shows the socket 110 of measurement evaluation device 100 in greater detail. The socket 110 may be provided in a side wall of the measurement evaluation device 100 as illustrated in FIG. 1 or may be provide in a separate socket container that is electrically connectable to the measurement evaluation device 100.

The socket 110 comprises a plurality of pins 120 that is arranged in a pattern corresponding to the plurality of contacts 50 of the measurement device 10 such that when the measurement sample handling device 1 is inserted into the socket 110, at least a portion of the plurality of pins 120 comes into electrical contact with at least one of the plurality of contacts 50. The number of the plurality of pins 120 may be inferior, equal or superior to the number of contacts 50 of the measurement device 10. Thus, the same socket 110 and consequently the same measurement evaluation device 100 may be used with a plurality of different measurement devices 10. The measurement devices 10 may differ in the number of electrical contacts 50, for example due to additional sensors, like temperature, pH sensors or similar, that are integrated in the measurement device 10, or due to a different number of electrodes 65 for different applications of the measurement device 10. Although the number of electrical contacts 50 may vary, the number and shape of the holes 42 in the plug portion 40 might be adapted to the number and shape of pins 120 in the socket 110 in order to provide correct contact and positioning for each of the pins 120 when the measurement sample handling or measurement sample handling device 1 with the measurement device 10 is inserted into the socket 110.

The plurality of pins 120 may be made of electrical spring contacts in order to ensure the contact of the plurality of pins 120 with the corresponding ones of the plurality of electrical contacts 50 when the measurement device 100 is inserted into the socket 110. The spring contacts may recede and thus prevent damage on the measurement device 10, when the measurement device 10 is inserted into the socket 110 and the electrical contacts 50 are forced against the pins 120.

The plurality of pins 120 may be arranged inside the socket 110 as illustrated in FIG. 6. Thus, when the measurement sample handling device 1 or solely measurement device 10 is introduced into the socket 110, the measurement device 10 is completely or partially positioned inside the socket 110. In this case no modification to the sample on the measurement surface is possible after the measurement is started and no electric contacts are necessary in the handling unit 200 while keeping the measurement device 10 small and therefore cheap In addition, a direct electrical connection with a patient or other user is impossible. Therefore the measurement device can be safely used by a patient or other user without specific training or care. This is important because high voltages, e.g. in the range or 1000 Volts may be used during measurement of the sample.

The measurement evaluation device 100 may only start a measurement when the measurement sample handling device 1 with the measurement device 10 is inserted correctly into socket 110. For example, a measurement may only be started if the required ones of the contacts 50a to 50i are actually in contact with the corresponding pins.

The actual measurement may only be started after successful control measurements are carried out in order to ensure correct operation of the measurement device 10. A control measurement may be for example measuring the sodium concentration in the liquid sample 5. The sodium concentration may be measured and evaluated substantially in parallel to the actual measurement of the lithium concentration. For a successful control measurement, the sodium concentration has to be in a range corresponding to that which is usually found in blood. In case a different sodium concentration is evaluated, something went wrong in the measurement and it can not be ensured that the evaluated lithium concentration is correct. The measurement would therefore be ignored.

Additional and initial controls can be performed, for instance measuring the conductivity or the temperature of the background electrolyte solution (BGE), in order to check the correctness of for example sodium concentrations.

Figure 8A:
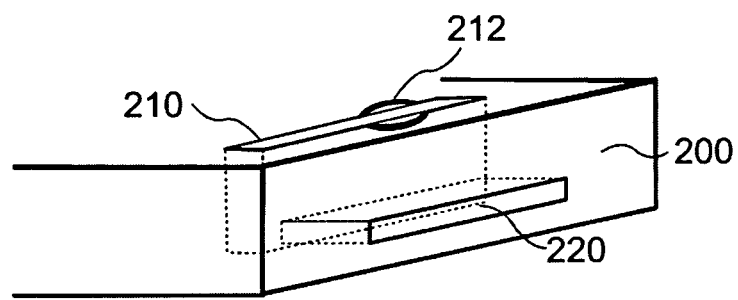
FIGS. 8a and 8b shows a finger tip positioning tool on the handling unit and a plurality of opening and control electrodes at the opening.

FIG. 8a shows a specific embodiment of the invention with a finger tip positioning tool integrated in the handling unit 200 described in detail above with respect to FIGS. 2a to 2c. A rim 212 is provided on one or more sides of the first opening 210 in the measurement side 202 of the handling unit 200. The rim 212 has the shape and height that it can easily be felt and or seen by a user (patient) using the measurement sample handling device 1 when putting a finger on top of the measurement side 202. The rim 212 may be arranged along the first opening 210 around the position, at which the opening 25 is located when the measurement device 10 is inserted into the handling unit 200. The rim 212 may thus serve as a positioning tool for depositing a liquid or blood sample onto the opening 25 at the measurement surface 20, as it may be felt by the finger tip of a user or because the rim may be simply seen by eye. This is in particular useful because the opening 25 itself may be too small to be seen by the user (patient) by eye.

A cavity or groove in the measurement surface 20 may also be used as positioning tool. The cavity or groove has the further advantage that the cavity or groove serves as collector for sample liquid and that can prevent sample liquid from leaking or spreading onto the measurement device.

Figure 8B:
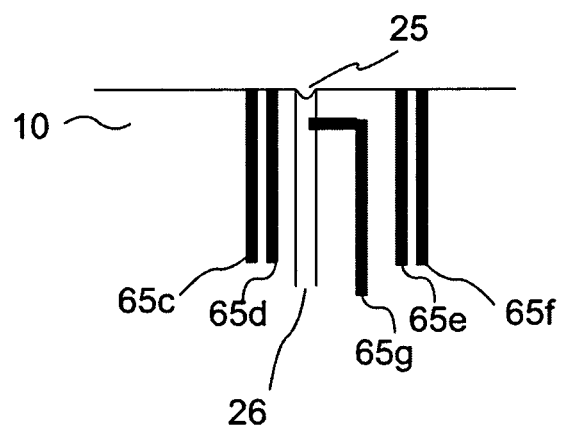

The opening electrode 56c, present at the first opening 25 as illustrated in FIG. 4 or FIG. 8b, may be used to detect the presence of sample liquid on or around the first opening 25. For example, the opening electrode 65c can be present at a certain position or height within the positioning cavity or groove. Thus the presence of a sample liquid 5, and moreover, the presence of a certain amount of sample liquid can be checked in order to ensure that the required amount of sample liquid has been added, that is necessary for reliable measurements.

FIG. 8b shows an example how additional electrodes can be arranged at the first opening 25. In addition to the opening electrode 65c, at least one control electrode 65d, 65e, and 65f can be used. The at least one control electrode 65d, 65e, 65f can be arranged close to the first opening 25, for measuring additional parameters such as conductivity of the liquid sample. For example, the conductivity of a liquid sample can be measured between the control electrode 65d and the control electrode 65e. The electrode 65f can be from a different material or can have a coating for measuring a different parameter of the liquid sample.

A channel electrode 65g may be provided in proximity to the first opening 25. The channel electrode 65g is in contact with the solution inside the sample channel 26, when the sample channel is filled with an electrolyte solution. In case evaporation of the electrolyte solution should occur, the level of the electrolyte solution would sink below the channel electrode 65g, which can be easily detected by conductivity measurements.

The channel electrode 65g as well as the opening electrode 65c and the control electrodes 65d, 65e, and 65f can thus be used for initial control measurements as for instance as indication for initial conductivity or evaporation and or gas bubble detection.

The opening electrode 65c or the control electrode 65d, 65e or 65f or the channel electrode 65g may also be used as electrophoresis electrode, for example for capillary electrophoresis inside the sample channel 26.

Figure 9:
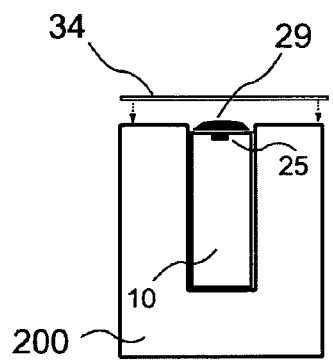
FIG. 9 shows a cross sectional view of the handling unit with the measurement device inserted and a sealing droplet.

FIG. 9 shows a cross sectional view of the handling unit 200 with the measurement device 10 inserted. Prior to use, a sealing droplet 29 may be placed at least on top of the opening 25. The sealing droplet 29 may be from silicone, PDMS or other material and covers the opening 25 and thus the microfluidic channel 60 in order to prevent evaporation and contamination. The sealing 34, described above with respect to FIG. 2a, may be a sticky foil for covering the measurement surface prior to use. The sealing droplet 29 may stick to the sticking foil. The user (patient) may remove the sticky foil and in the same time the sealing droplet 29 sticking to it, thereby providing access to the opening 25.

Figure 10A:
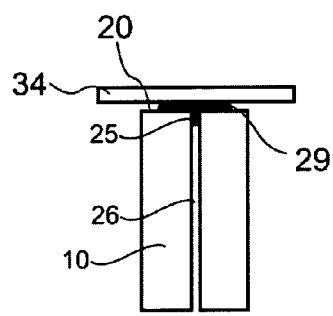
FIGS. 10a to 10c show variants of the sealing and a sealing droplet attached to the measurement device.
Figure 10B:
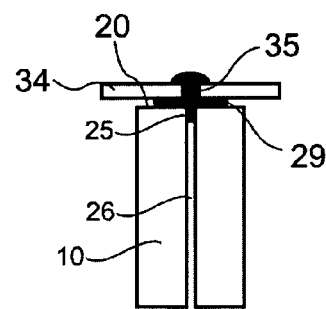
Figure 10C:
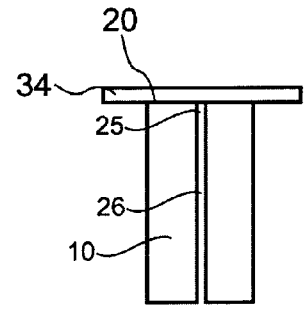

FIGS. 10a to 10c show different arrangements of the sealing 34 and the sealing droplet 29 on the first opening 25 of measurement device 10. As illustrated in FIG. 10a, a sealing droplet 29, that may be from silicon material or the like, may be placed on the first opening 25 after the microfluidic network comprising the microfluidic channel 60 and the sample channel 26 has been filled with a liquid prior to use of the measurement device 10. The sealing droplet 29 thus prevents any evaporation of liquid from the microfluidic network through the first opening 25. A further sealing 34, for example in form of a tape or foil may be applied on top of sealing droplet 29. When a patient or user wants to use the measurement device 10, he removes the sealing 34 and the sealing droplet 29 away, before applying the liquid sample 5 to the first opening 25. The sealing droplet 29 may be attached to the sealing 34 in order to facilitate its removal.

The sealing 34 may also comprise a hole 35 aligned substantially on top of the first opening 25 when the sealing 34 is placed on the measurement surface 20 of measurement device 10 as illustrated in FIG. 10b. In this case, the sealing droplet 29 may extend through the hole 35 in the sealing 34 for secure attachment. Thus the sealing droplet 29 is removed form the first opening 25 when a user or patient removes the sealing 34 prior to use of the measurement device 10.

The sealing 34 may also be directly attached to the measurement surface 20 of measurement device 10. The sealing 34 may thus directly seal the first opening 25. The sealing may be a tape or a foil, made from or covered by silicone or other suitable material.

The sealing 34 and eventually the sealing droplet 29 may also be attached to the closure device 30. In this case, the sealing is removed when the closure device 30 is opened prior to use of the measurement device 10. The sealing may also be applied when closing the closure device 30 after placing the liquid sample 5 on the measurement surface 20 in order to prevent contamination and evaporation of the liquid sample 5.

A person skilled in the art will understand that the sealing 34 described above with respect to the first opening 25 can also be applied to further openings in the measurement device 10, for example to the second opening 27 illustrated describe with respect to in FIG. 5.

Figure 11:
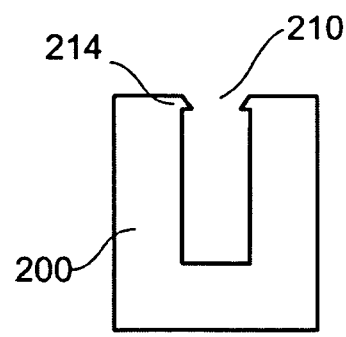
FIG. 11 shows the handling unit with a locking device for fixing the measurement device in the handling unit.

FIG. 11 shows the handling unit 200 of the present invention with a locking device 214 for fixing the measurement device 10 in the handling unit 200. The measurement device 10 may be inserted through first opening 210 into handling unit 200, as illustrated in FIG. 2a. A locking device 214 in form of a rim may be provided at the opening 210. Thus, the width of the opening 210 in at least one direction may be somewhat smaller or equal to the corresponding size of the measurement device 10. The locking device 214 may serve as a fixation or snap-in mechanism for the measurement device 10 in the handling unit 200.

Figure 12A:
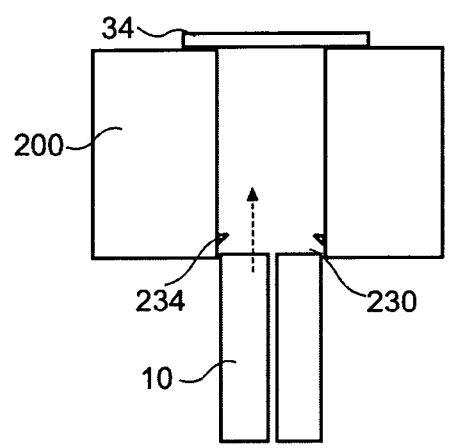
FIGS. 12a and 12b show the insertion of measurement device into the handling unit through a third opening in the handling unit.
Figure 12B:
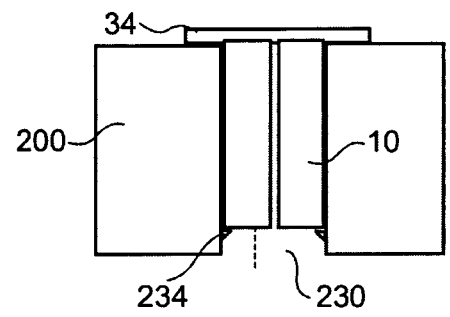

FIGS. 12a and 12b shows the insertion of measurement device 10 into the handling unit 200 through a third opening 230 provided in the handling unit 200. The third opening may be provided on an opposite side to first side 202 of handling unit 200. Thus, the first opening 210 in handling unit 200 can be smaller in size and provide essentially only access to the first opening 25 on the measurement surface 20. In this way, the contact seal for preventing sample liquid form coming into contact with the plug portion 40 can be substantially large in size. Furthermore, positioning of the measurement surface 20 and the first opening 25 can be carried out more precisely.

The third opening 230 may also be combined with the second opening 220 to form one enlarged opening for the plug portion 40 and the insertion of the measurement device 10.

Figure 13:
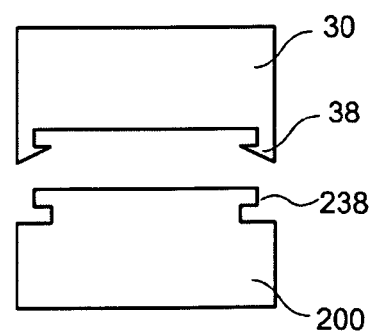
FIG. 13 shows a locking mechanism for closing the handling unit with the closure device.

A locking device 234 that may be snap-in mechanism is provided at handling unit 200 and/or measurement device 10 in order to ensure fixation and correct positioning of the measurement device 10 inside the handling unit 200, as illustrated in FIG. 12b. The seal 34, the permeable layer 32 or other means provided in the handling unit 200 may provide a counterforce for when the measurement device 10 is inserted to ensure the closure of the first opening 25 in order to prevent contamination and evaporation FIG. 13 shows a locking mechanism for closing the handling unit 200 with the closure device 30. The closure device 30 may be provided with a hook 38, that may engage with a corresponding notch 238 at the handling unit 200, when the closure device 30 is positioned on the first surface 202 of handling unit 200 in order to cover and protect the measurement surface 20 and opening 25, in particular after a liquid sample has been placed on the opening 25 of the measurement device 10. The hook 38 and the notch 238 may engage with each other in non-removable manner forming a snap-in locking device. In this case, after closing the closure device 30, the handling unit 200 can not be reopened and thus not be reused. This prevents contamination of the sample as well as falsification of the measurement results.

It is obvious that other snap-in or locking mechanisms can be used with the invention. For example, the locking mechanism may be provided as a mechanism that can be opened and closed several times for allowing multiple access to the measurement surface. Such mechanisms are commonly known and widely used.

The invention has been described with respect to several embodiments. It will, however, be clear to those skilled in the art that the invention is not limited thereto. Rather the scope of the invention is to be interpreted in conjunction with the following claims.

The invention claimed is:

1. A measurement sample handling device comprising a handling unit and a measurement device for taking a liquid sample, the measurement device comprising:
   at least one channel, the at least one channel being filled with a solution prior to use;
   a measurement portion with a measurement surface for being in use contacted with the liquid sample, wherein the measurement portion comprises at least one first channel opening providing access to the at least one channel in the measurement device;
   a plug portion having a plurality of electrical contacts, wherein the plug portion is mountable to a socket of a measurement evaluation apparatus,
   the handling unit having:
   at least a first opening,
   at least a second opening, and
   a removable seal for preventing leakage of the solution from the at least one channel, wherein the seal is removable by a user prior to the use of the measurement device
   wherein the first opening provides access to the measurement surface for placement of the liquid sample after insertion of the measurement device, the second opening provides access to the electrical contacts after insertion of the measurement device, and the first opening and the second opening are so arranged that, after insertion of the measurement device, the handling unit provides an electrical contact seal for sealing the measurement surface from at least one of the plurality of electrical contacts; and
   wherein the measurement sample handling device comprises means for preventing evaporation comprising a second channel opening fluidly connected to the at least one first channel opening.

2. The measurement sample handling device of claim 1, wherein the plug portion is located on a different side of the measurement device with respect to the measurement surface.

3. The measurement sample handling device of claim 1, wherein the measurement device is at least partially made from glass material.

4. The measurement sample handling device of claim 1, further comprising electrodes arranged along the at least one channel.

5. The measurement sample handling device of claim 4, wherein the electrodes comprise conductivity electrodes.

6. The measurement sample handling device of claim 4, wherein the electrodes comprise electrophoresis electrodes.

7. The measurement sample handling device of claim 4, wherein the electrodes comprise at least one opening electrode for measuring the presence of sample liquid at the at least one first channel opening.

8. The measurement sample handling device of claim 7, wherein the at least one opening electrode is adapted for measuring at least one parameter of the sample liquid.

9. The measurement sample handling device of claim 4, wherein the electrodes comprise at least one control electrode for measuring at least one parameter in a supply channel.

10. The measurement sample handling device of claim wherein the second channel opening is substantially larger in size than the at least one first channel opening.

11. The measurement sample handling device of claim 1, wherein the measurement portion and the plug portion are realized in one piece.

12. The measurement sample handling device of claim 1, wherein the liquid sample is a sample of a body fluid.

13. The measurement sample handling device of claim 1, wherein the measurement device is adapted to measure lithium in the liquid sample.

14. The measurement sample handling device of claim 1, further comprising a temperature sensor.

15. The measurement sample handling device of claim 1, further comprising non-active electrical elements.

16. The measurement sample handling device of claim 1, wherein the handling unit is substantially larger in size than the measurement device.

17. The measurement sample handling device of claim 1, wherein the measurement portion of the measurement device is located inside the handling unit.

18. The measurement sample handling device of claim 1, further comprising a third opening for inserting of the measurement device into the handling unit.

19. The measurement sample handling device of claim 1, further comprising a measurement device locking mechanism for locking the measurement device in the handling unit.

20. The measurement sample handling device of claim 1, wherein the measurement surface is substantially concealable by a closure device.

21. The measurement sample handling device of claim 20, further comprising the removable seal between the closure device and the measurement surface for substantially sealing the measurement surface from surroundings.

22. The measurement sample handling device of claim 20, wherein the closure device is substantially larger in size than the measurement surface.

23. The measurement sample handling device of claim 1, wherein the handling unit and the closure device are realized in one piece.

24. The measurement sample handling device of claim 1, further comprising a closure device locking mechanism for concealing the measurement surface with the closured device.

25. The measurement sample handling device of claim 1, wherein at least one geometrical parameter of the handling unit is adapted to fit into the socket.

26. A measurement sample handling device comprising a handling unit and a measurement device for taking a liquid sample, the measurement device comprising:
- at least one channel, the at least one channel being filled with a solution prior to use;
- a measurement portion with a measurement surface for being in use contacted with the liquid sample, wherein the measurement portion comprises:
  - a first channel opening providing access to the at least one channel in the measurement device;
  - a second channel opening for modifying evaporation behavior at the first channel opening, wherein the second channel opening is fluidly connected to the at least one first channel opening, wherein the second channel opening is substantially larger in size than the first channel opening so that the level of liquid in the first channel opening remains at a generally constant level when liquid evaporates from the first and second openings;
- a plug portion having a plurality of electrical contacts, wherein the plug portion is mountable to a socket of a measurement evaluation apparatus, the handling unit having:
  - at least a first opening,
  - at least a second opening, and
  - a removable seal for preventing leakage of the solution from the at least one channel, wherein the seal is removable by a user prior to the use of the measurement device
  wherein the first opening provides access to the measurement surface for placement of the liquid sample after insertion of the measurement device, the second opening provides access to the electrical contacts after insertion of the measurement device, and the first opening and the second opening are so arranged that, after insertion of the measurement device, the handling unit provides an electrical contact seal for sealing the measurement surface from at least one of the plurality of electrical contacts.

27. The measurement sample handling device of claim 26, wherein the difference in size between the first channel opening and the second channel opening results in a difference of pressure in the first opening and in the second opening thereby modifying the evaporation behavior at the first channel opening.

\* \* \* \* \*